United States Patent [19]

Tachibana

[11] Patent Number: 5,247,179

[45] Date of Patent: Sep. 21, 1993

[54] ACTIVATION ENERGY PROVIDING DEVICE

[76] Inventor: Hiroshi Tachibana, 14-31 Kugayama 3-chome, Suginami-ku, Tokyo, Japan

[21] Appl. No.: 777,789

[22] Filed: Oct. 17, 1991

[30] Foreign Application Priority Data

Oct. 18, 1990 [JP] Japan ................................. 2-281236
Aug. 23, 1991 [JP] Japan ................................. 3-237161

[51] Int. Cl.$^5$ .............................................. H01J 37/00
[52] U.S. Cl. ................................ 250/492.1; 250/455.11
[58] Field of Search ..................... 250/492.1, 455.11

[56] References Cited

U.S. PATENT DOCUMENTS

| | | | |
|---|---|---|---|
| 1,844,420 | 2/1932 | Buttolph | 250/492.1 |
| 2,208,578 | 7/1940 | Haddad | 250/455.11 |
| 3,306,835 | 2/1967 | Magnus | 250/492.1 |
| 4,121,107 | 10/1978 | Bachmann | 250/492.1 |
| 4,304,996 | 12/1981 | Blades | 250/455.11 |
| 4,976,920 | 12/1990 | Jacob | 250/492.1 |
| 5,012,110 | 4/1991 | Kropp | 250/492.1 |

*Primary Examiner*—Paul M. Dzierzynski
*Assistant Examiner*—Kiet T. Nguyen
*Attorney, Agent, or Firm*—Townsend, Snider & Banta

[57] ABSTRACT

A target irradiating device including a magnetic force generating member for electrically generating a magnetic force; a power supplying member for supplying a driving power to the magnetic force generating member; a control member for controlling the power supplying member so that a voltage signal for periodically changing an intensity of the magnetic force is supplied from the power supplying member, the voltage signal having a lowering pattern in one cycle such that a bottom point of voltage maintained at a constant level; and an irradiating member for irradiating the magnetic force generated by the magnetic force generating member to a desired target. The target irradiating device may be adapted to a water treatment device for treating water as the desired target to obtain an irradiated water.

15 Claims, 11 Drawing Sheets

ACTIVATION ENERGY PROVIDING DEVICE

BACKGROUND OF THE INVENTION

The present invention relates to an target irradiating device, and more particularly to target irradiating device adapted to be used for water treatment or medical treatment, for example. In case of the water treatment, a target irradiating energy generated from the target irradiating device is irradiated to a city water, for example, to improve it in taste and biological or physiological aspects. In case of the medical treatment, the target irradiating energy is irradiated to a living body such as a human body to cure or prevent some kind of affection.

In recent years, the existence of Chinese "Ki" to be exerted from the hands of a so-called "Kikoshi" has been noticed. The term of "Ki" is considered as an electromagnetic wave such as far infrared radiation to be radiated from a surface of a human body, especially, his hands. This electromagnetic wave has an intensity more than a certain level and has a specific wave form pattern. Thus, such an electromagnetic wave is radiated more or less, but it is positively radiated from the hands of a special person called "Kikoshi" who has an ability of generating the above specific electromagnetic wave in nature or by skill. In particular, "Ki" has been remarkably studied in China, and it is especially applied to a medical field where the specific electromagnetic wave generated from "Kikoski" is radiated against affection such as shoulder stiffness, lumbago or neuralgia to actually exhibit some effects for a remedy of such affection.

The target irradiating device of the present invention is designed to scientifically or technically generate target irradiating energy like the Chinese "Ki" to make same useful for water treatment and medical treatment, for example. Concretely, target irradiating energy to be provided by the present invention is a magnetic force and/or light with its intensity periodically changed.

In the case that the present invention is applied to water treatment, it is possible to obtain an irradiated water which has been unobtainable in the prior art.

As a conventional water treatment device, a water purifier for improving a quality of a city water has been recently developed for home use. It is known that such a water purifier utilizes a ceramic filter, hollow yarn film, or electrolysis, and that it is directly connected to a faucet. By using the water purifier, a bleaching powder smell in the city water can be reduced to provide a drinking water improved in quality.

Incidentally, water exists in the state that at least five molecules of water are gathered to form a so-called cluster rather than in the state of a single molecule. A, although the above-mentioned water purifier of the filter type or the electrolysis type has a function of reducing a bleaching powder smell in the city water or improving a taste of the city water, it cannot change a characteristic of the water in a biological or biochemical level. That is, it cannot create an activated water having a large biological or biochemical effect on animals (inclusive of a human body) and plants.

As to the medical treatment for a living body, some kind of affection such as stiffness of shoulders, lumbago, or neuralgia cannot be perfectly cured even by dozing a large quantity of medicine. However, it has been confirmed in the Oriental medicine that such affection can be remarkably cured by applying the aforementioned "Ki" to an effective spot on a living body.

SUMMARY OF THE INVENTION

It is an object of the present invention to provide target irradiating device which can provide target irradiating energy like the Chinese "Ki" and can be applied to water treatment for providing an irradiated water effective in various aspects such as physiology, food processing, growth of plants and animals, suppression of putrefaction, or activation of cells.

It is another object of the present invention to provide a target irradiating device which can be applied to medical treatment effective for a remedy in a living body such as a human body.

According to a first aspect of the present invention, there is provided a target irradiating device comprising magnetic force generating means for electrically generating a magnetic force; power supplying means for supplying a driving power to said magnetic force generating means; control means for controlling said power supplying means so that a voltage signal for periodically changing an intensity of said magnetic force is supplied from said power supplying means, said voltage signal having a lowering pattern in one cycle such that a bottom point of voltage gradually lowers in terms of time with a top point of voltage maintained at a constant level and an irradiating member for irradiating said magnetic force generated by said magnetic force generating means to a desired target.

With this construction, the magnetic force generated by the magnetic force generating means with the intensity thereof periodically changed is irradiated from the irradiating member to the desired target such as water. In case of treating water according to the present invention, the cluster of the water can be enlarged by the irradiation of the magnetic force to the water. For example, the cluster as a group of about five molecules of water is changed into a large cluster as a group of tens of molecules of water. This phenomenon is contrary to the aforementioned phenomenon that the conventional water purifier functions to reduce the cluster of the water. The treated water having such a large cluster obtained by the target irradiating device can favorably affect as an activated water in biological or biochemical aspect.

According to a second aspect of the present invention, there is provided a target irradiating device comprising light generating means for electrically generating light; power supplying means for supplying a driving power to said light generating means; control means for controlling said power supplying means so that a voltage signal for periodically changing an intensity of said light is supplied from said power supplying means, said voltage signal having a rising pattern in one cycle such that a bottom point of voltage gradually rises in terms of time with a top point of voltage maintained at a constant level; and an irradiating member for irradiating said light generated by said light generating means to a desired target.

With this construction, substantially the same effect as that mentioned above can be obtained.

According to a third aspect of the present invention, there is provided a target irradiating device comprising magnetic force generating means for electrically generating a magnetic force; light generating means for electrically generating light; power supplying means for supplying a driving power to said magnetic force generating means and said light generating means; control means for controlling said power supplying means so that an intensity of said magnetic force to be generated by said magnetic force generating means and an intensity of said light to be generated by said light generating means are periodically changed; and an irradiating member for irradiating said magnetic force generated by said magnetic force generating means and said light generated by said light generating means to a desired target.

With these constructions, substantially the same effects as those mentioned above can be obtained.

Other objects and features of the invention will be more fully understood from the following detailed description and appended claims when taken with the accompanying drawings.

DETAILED DESCRIPTION OF THE PREFERRED EMBODIMENTS

Figures 1, 2:
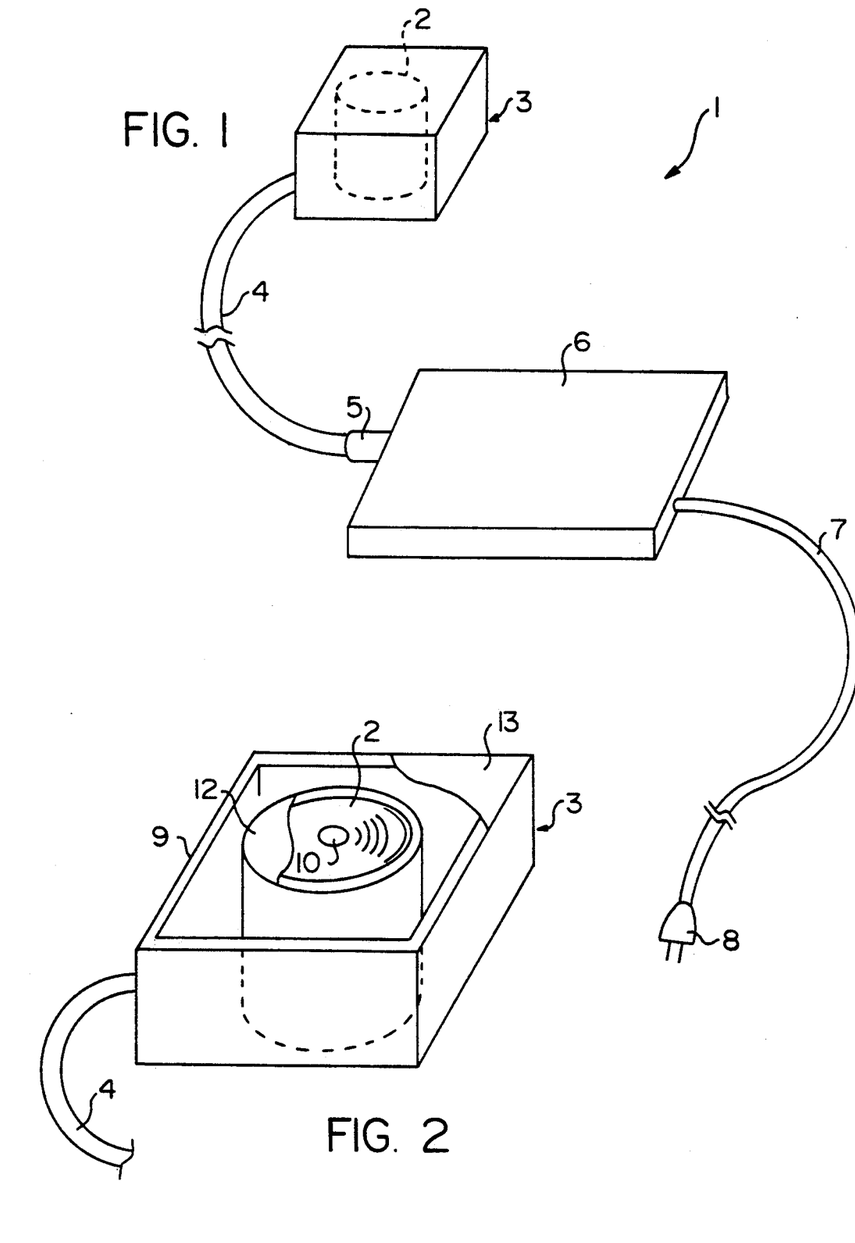
FIG. 1 is a general perspective view of a water treatment device according to a first preferred embodiment of the present invention.
FIG. 2 is a perspective view of a body of the water treatment device shown in FIG. 1.

Referring now to FIG. 1, reference numeral 1 generally denotes a water treatment device functioning as the target irradiating device according to a first preferred embodiment of the present invention. The water treatment device 1 includes a body 3 which incorporates a coil 2, and an electronic control unit 6 (which will be hereinafter referred to as a control unit 6) connected through a cord 4 and a connector 5 to the body 3. The control unit 6 is provided with a cord 7 having a plug socket 8 at a free end thereof, which plug socket 8 is adapted to be connected to an AC power source.

Referring to FIG. 2, the body 3 is provided with a box-shaped case 9, in which the coil 2 is fixedly mounted. The coil 2 functions as the magnetic force generating means according to the present invention. The coil 2 is constructed by winding a conductive wire about an iron core 10 by 2000 turns to constitute an electromagnet. An upper end surface of the coil 2 is covered with a covering film 12 made of synthetic resin. Further, an upper opening of the case 9 is covered with a cover 13 having a magnetic permeability. The coil 2 is fixed in the case 9 so that when the case 9 is placed on a horizontal plane, the iron core 10 is directed in a substantially vertical direction, i.e., there is generated a line of magnetic force directed upwardly. The cover 13 provided on the upper surface of the case 9 forms a flat surface on which a water container or the like is to be placed, and the flat surface functions as a magnetic force irradiating member.

Figure 3:
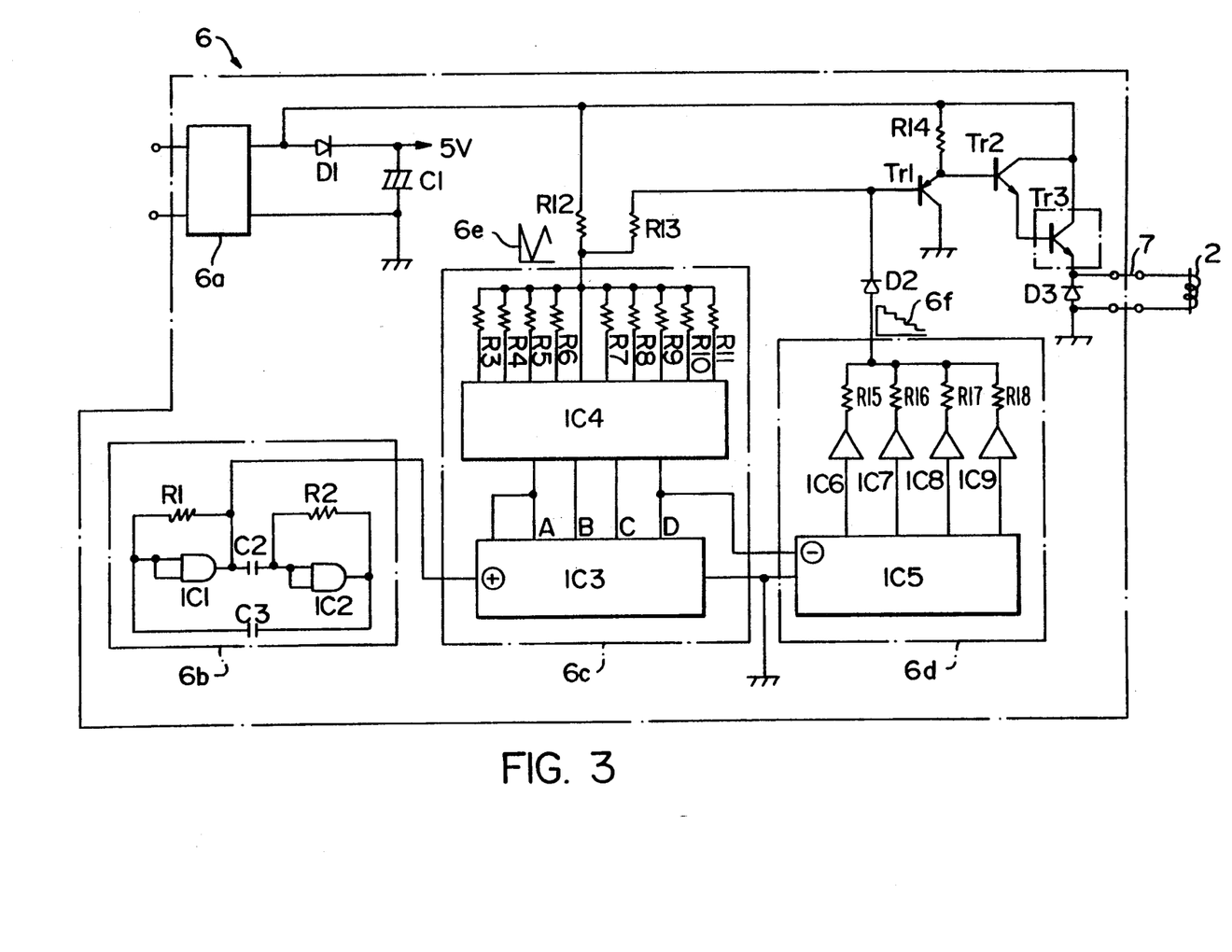
FIG. 3 is a circuit diagram of a control unit of the water treatment device shown in FIG. 1.

Referring next to FIG. 3 which shows a circuit construction of the control unit 6 for controlling a driving power (voltage) for the coil 2, the control unit 6 includes an oscillator circuit 6b consisting of digital integrated circuits IC1 and IC2, resistors R1 and R2, and capacitors C2 and C3. The oscillator circuit 6b generates pulses of a desired frequency.

The control unit 6 further includes an analog signal generator circuit 6c consisting of a counter integrated circuit IC3, an analog voltage generating integrated circuit IC4, and resistors R3 to R11. The analog signal generator circuit 6c generates a triangular wave voltage signal 6e.

The control unit 6 further includes a step form wave generator circuit 6d consisting of a counter integrated circuit IC5, amplifiers IC6 to IC9, and resistors R15 to R18. The step form wave generator circuit 6d generates a step form wave voltage signal 6f having a lowering pattern or a rising pattern.

The triangular wave voltage signal 6e and the step form wave voltage signal 6f are added together, and the sum of these voltages is in turn applied to a base of a transistor Tr1. Then, the transistor Tr1 changes an internal resistance in accordance with the voltage applied to the base thereof.

The transistor Tr1 is connected to a transistor Tr2. The transistor Tr2 is connected by Darlington connection to a transistor Tr3 to form an output transistor. The transistor Tr2 is driven by the transistor Tr1, and the transistor Tr3 is driven in accordance with a change in internal resistance of the transistor Tr2. The transistor Tr3 is connected in series with the coil 2. A current flowing in the coil 2 is adjusted by the transistor Tr3. Further, a diode D3 is provided to protect the transistor Tr3 from a reverse electromotive force of the coil 2. The control unit 6 further includes a power supply circuit 6a for converting a power of AC 100 V into a constant-voltage power.

Figure 6A:
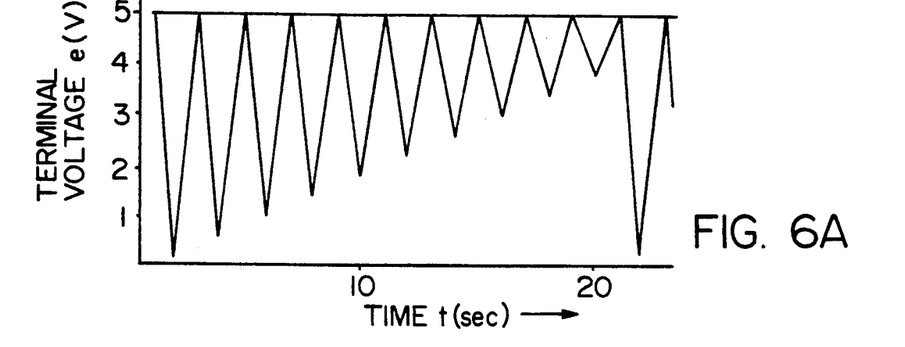
FIGS. 6A to 6D are graphs illustrating various patterns of a driving voltage signal to be applied to a coil in the body of the water treatment device shown in FIG. 1.
Figure 6B:
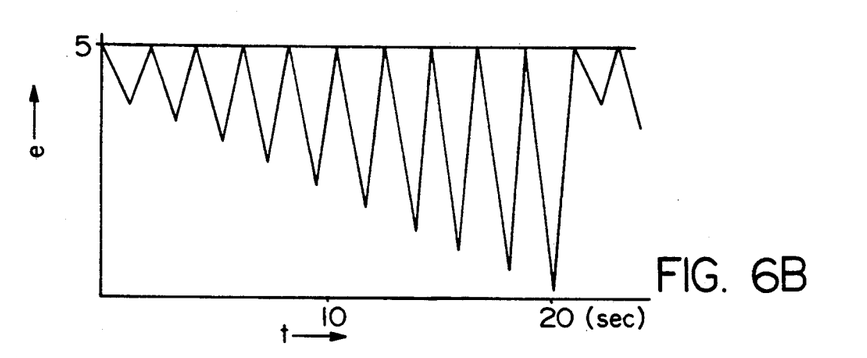
Figure 6C:
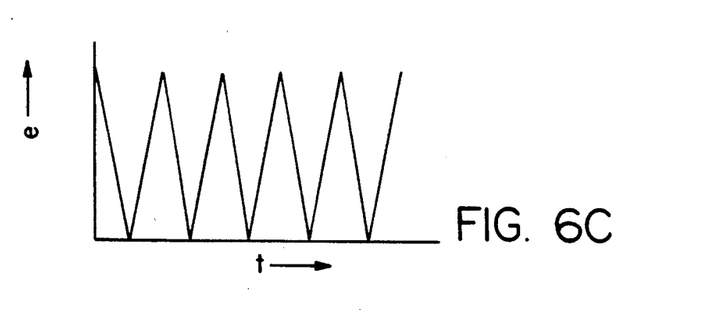
Figure 6D:
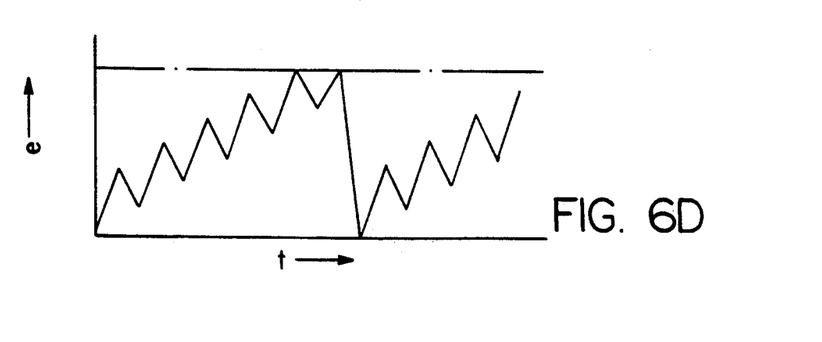

In case of forming a step form wave of a rising pattern in the step form wave generator circuit 6d, the step form wave from the circuit 6d is synthesized with the continuous triangular wave from the circuit 6c to form a saw-toothed wave of a rising pattern as shown in FIG. 6A such that for example, a peak point is kept constant at 5 V and a bottom point is stepwise raised. Such a saw-toothed wave of a rising pattern is repeatedly generated at predetermined intervals. An output voltage wave pattern from the control unit 6 is not limited to that shown in FIG. 6A, but various patterns as shown in FIGS. 6B to 6D may be formed by suitably varying a circuit constant.

Figure 4:
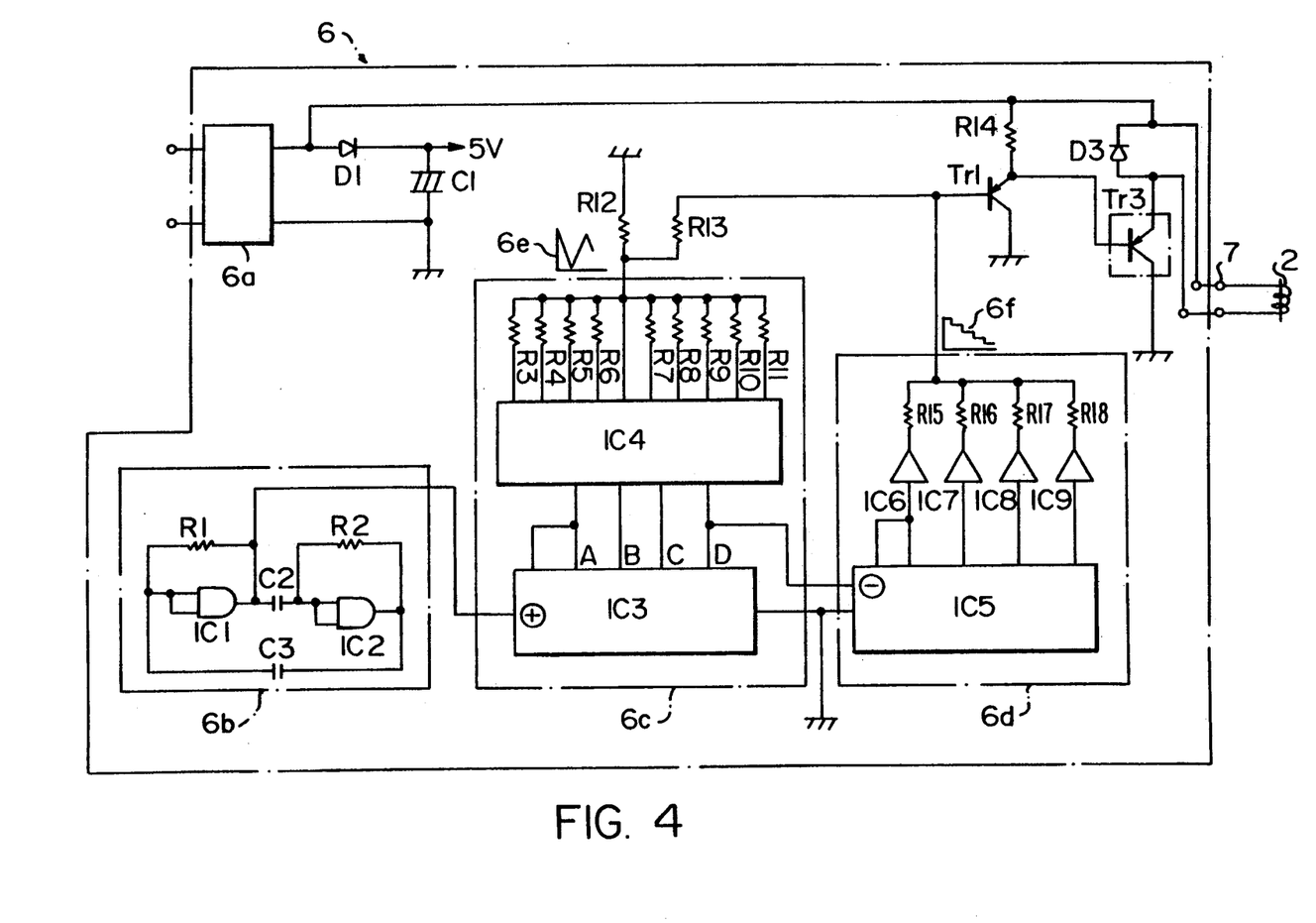
FIG. 4 is a circuit diagram of a modification of the control unit.

The circuit construction of the control unit 6 may be modified as shown in FIG. 4 in such a manner that a resistor R12 is grounded and the transistor Tr2 shown in FIG. 3 is eliminated with the diode D3 connected as shown.

Figure 5:
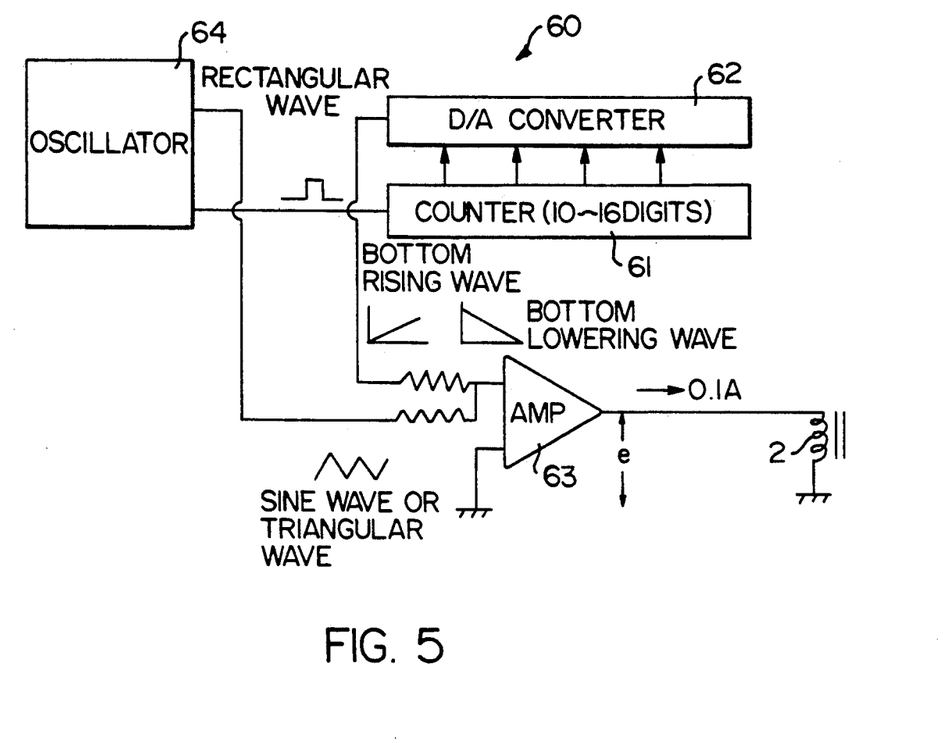
FIG. 5 is a block diagram of a further modification of the control unit.

Further, the circuit construction of the control unit 6 may be modified as shown in FIG. 5. Reference numeral 60 denotes a control unit including an oscillator (function generator) 64, a 10-16 digits counter 61, a D/A converter 62, and an amplifier 63. The oscillator 64 generates a triangular wave or a sine wave, and also generates a rectangular wave (10-16 waves). The rectangular wave is input into the counter 61 and then fed to the D/A converter 62, thereby obtaining a step form wave of a lowering pattern or a rising pattern. Then, the step form wave is synthesized with the triangular wave or the sine wave output from the oscillator 64, and is then amplified by the amplifier 63, thereby obtaining a voltage waveform as shown in FIG. 6A or 6B. The output voltage from the amplifier 63 is applied to the coil 2 to drive the same. A maximum current flowing in the coil 2 is set to about 0.1 A, for example.

Figure 7:
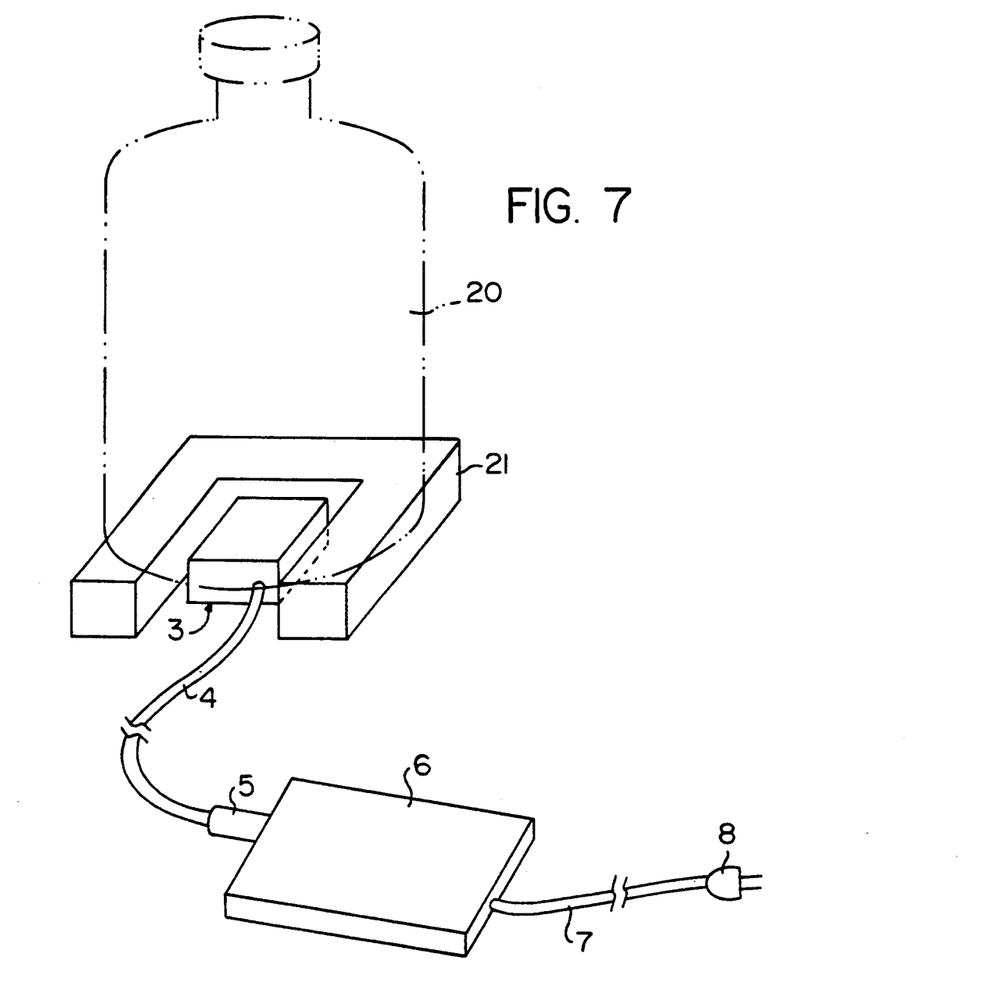
FIG. 7 is a perspective view illustrating a manner of usage of the water treatment device shown in FIG. 1.
Figure 8:
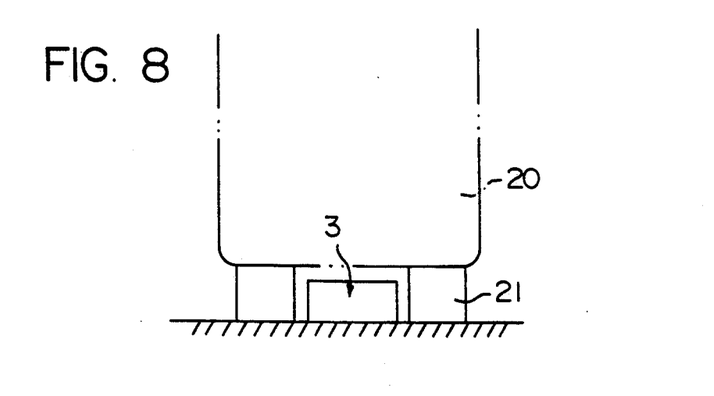
FIG. 8 is an elevational view of a part of FIG. 7.

The water treatment device 1 as constructed above is used as shown in FIGS. 7 and 8, for example. Referring to FIGS. 7 and 8, the body 3 of the water treatment device 1 is placed on a horizontal plane, and a water container 20 made of glass or synthetic resin is put on the upper surface of the body 3. In the case that an area of the bottom of the water container 20 is larger than that of the upper surface of the body 3, an assisting base 21 having a height slightly larger than that of the body 3 is placed on the horizontal plane so as to surround the body 3, and the water container 20 is placed on the assisting base 21. In this condition, an exciting voltage as shown in FIG. 6A, for example, is applied through the control unit 6 to the coil 2 in the body 3, so that a magnetic force of a pattern corresponding to the voltage waveform as shown in FIG. 6A is irradiated through the bottom of the water container 20 to the water contained therein.

Figure 9A:
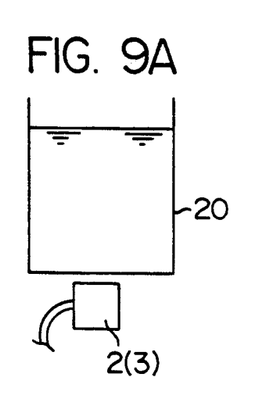
FIGS. 9A to 9C are schematic elevations illustrating various manners of stirring of water to be treated by the water treatment device.
Figure 9B:
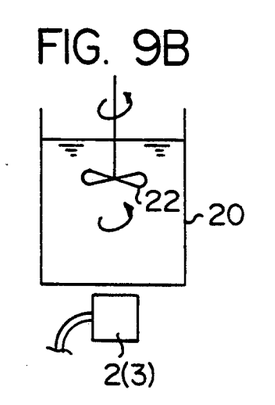
Figure 9C:
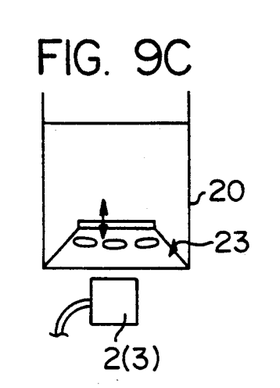

The water treatment is carried out with the water in the water container 20 standing still as shown in FIG. 9A or with the water being stirred as shown in FIG. 9B or 9C.

As shown in FIG. 9A, the water in the water container 20 is treated under the condition of natural convection. In the case that the quantity of the water is about 1.5 liters, a time for the water treatment is set to about 2 hours.

As shown in FIG. 9B, a stirring screw 22 as the stirring means in the present invention is provided so as to be rotated in the water container 20 to forcibly stir the water. In this case, the time for the water treatment can be shortened as compared with the case shown in FIG. 9A.

Figure 10:
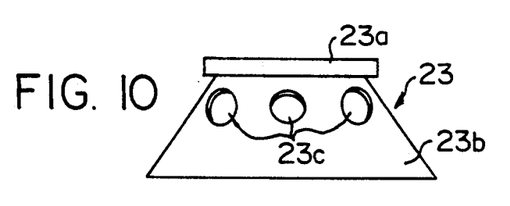
FIG. 10 is an enlarged elevational view of a diaphragm shown in FIG. 9C.

As shown in FIG. 9C, a diaphragm 23 as the stirring means in the present invention is provided in the water container 20 to forcibly stir the water. A construction of the diaphragm 23 is shown in FIG. 10. As apparent from FIG. 10, the diaphragm 23 is constructed of a waterproof movable plate 23a made of a ferromagnetic material such as iron and an elastic skirt member 23b formed of an elastic material such as rubber. The skirt member 23b is formed with a plurality of through holes 23c for permitting pass of the water. The movable plate 23a is separatably mounted on the top of the skirt member 23b, so that when the coil 2 is driven, the movable plate 23a is vertically moved by a magnetic field generated by the coil 2 to stir the water. In this case, the time for the water treatment can be shortened to about ⅓ as compared with the case shown in FIG. 9A.

The treated water obtained by using the water treatment device 1 was tested by an NMR spectroscopy. A structure or state of water in its molecular level can be observed without breaking the molecule of water by the NMR spectroscopy. That is, since water is represented as $H_2O$, the behavior of water in its molecular level can be grasped by observing a nuclear of hydrogen ($^1H$) or a nuclear of oxygen ($^{17}O$). As previously described, water exist in the state of a cluster as a group of at least five molecules rather than in the state of a single molecule. A life of the cluster (a change in magnitude thereof) is very short such as $10^{-12}$ seconds (one picosecond). In the test, the $^{17}O$-NMR spectroscopy for observing the nuclear of oxygen ($^{17}O$) was adopted to analyze and evaluate the treated water in comparison with an untreated water.

Water Analysis Test by NMR Spectrometry (1) Measurement (a) Water Used

A purified water of Japanese pharmacopoeia by Kyoei Yakuhin Kabushiki Kaisha was used.

(b) Samples Tested

The above purified water was used as the untreated water, while it was treated by the water treatment device 1 for 2 hours in the condition of natural convection to prepare a treated water.

(c) Elapsed Time from the Preparation of the Samples to the NMR Measurement

After 40 days from the preparation of the samples, the measurement was carried out.

(d) Measurement Conditions

Target Nuclear: $^{17}O$
Measuring Frequency: 36.6 MHz
Measuring Method: SGNON (Normal measuring method)
Pulse Width: $21\mu$ sec (90° pulse)
Repeating Time:
  ACQTM=0.102 sec
  PD=0.100 sec
Accumulation Times: 1000
Measuring Temperature: 20.0° C.

(2) Result

Figure 12:
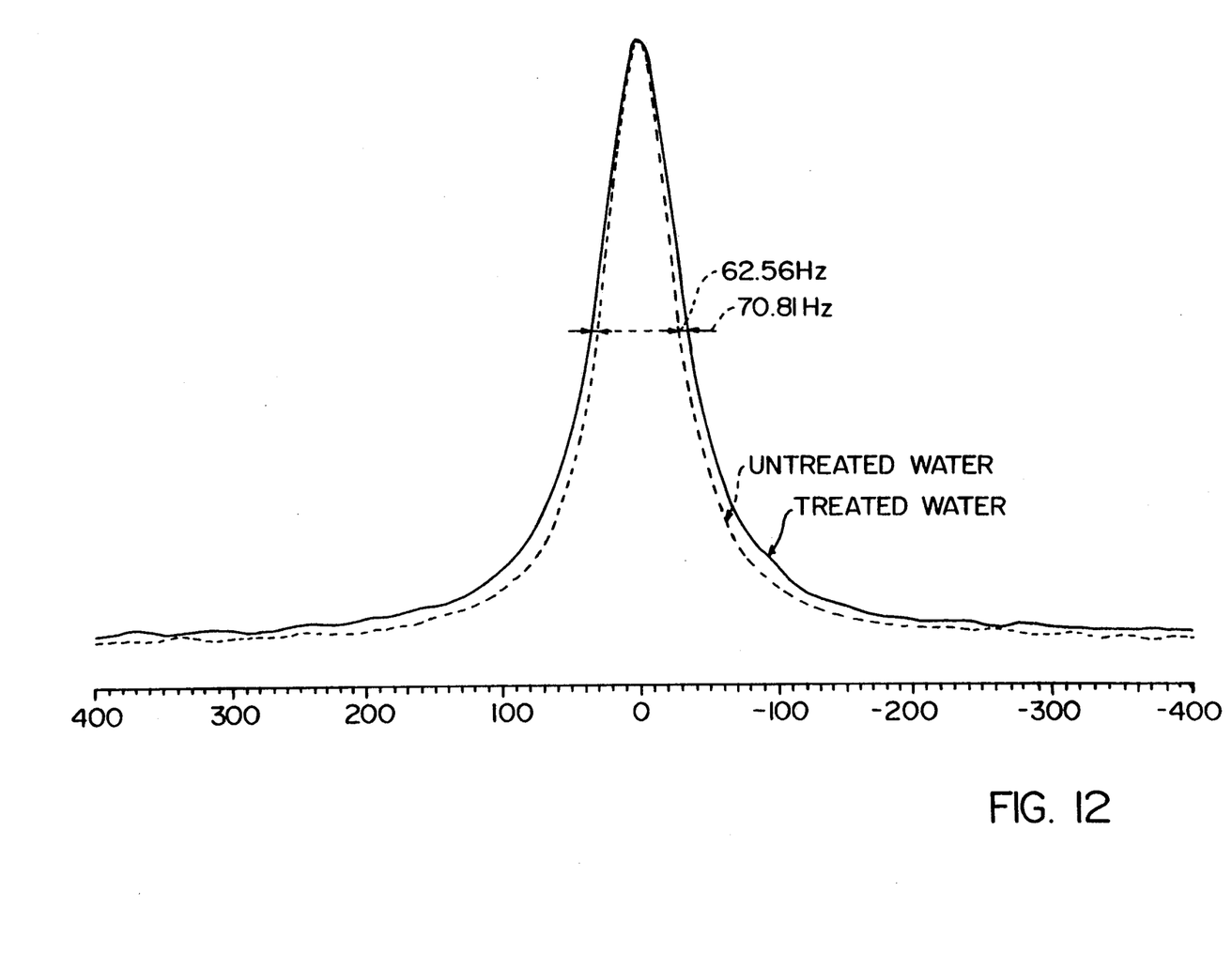
FIG. 12 is a graph illustrating spectrums obtained by an NMR spectroscopy for a treated water by the water treatment device and an untreated water.

The result of the above NMR spectrometry is shown in FIG. 12. Referring to FIG. 12, a dashed line represents an NMR spectrum of the untreated water, and a solid line represents an NMR spectrum of the treated water. As apparent from FIG. 12, a line width of the spectrum of the treated water is larger than that of the untreated water. That is, a half width of the spectrum of the untreated water is 62.56 Hz, and a half width of the spectrum of the treated water is 70.81 Hz. These values are intrinsic line widths of the untreated water and the treated water. Each line width is inversely proportional to a relaxation time which is a time for discharging an energy absorbed by the nuclear ($^{17}O$) used in the NMR spectrometry. Therefore, when the cluster as a group of water molecules becomes large to cause slowing of a molecule motion, the relaxation time is shortened to cause an increase in line width of NMR spectrum. As a consequence, the increase in line width means that a proportion of enlarged clusters in the treated water is increased in average.

In general, it is known that when a very weak external energy such as ultrasonic wave, radio wave, or low-frequency vibration is applied to water, bonding of water molecules constituting a cluster is broken to reduce a size of the cluster, and that a life of such a small cluster is short to restore an original condition in a short period of time by rebonding of the molecules.

In contrast, the test result proves that the water cluster is increased in size by irradiation of a magnetic force with use of the water treatment device 1, and that the large cluster obtained remains still even at the time 40 days have elapsed after treating the water.

Germination Test for Radish Sprouts with use of a Treated Water

Figure 11:
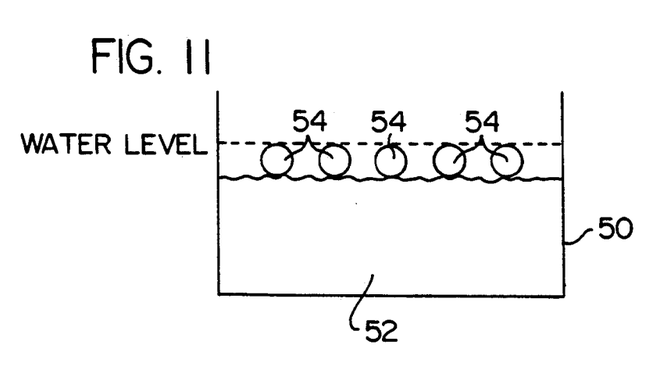
FIG. 11 is a schematic elevation of a seedling bed in a germination test of radish sprouts with use of a treated water obtained by the water treatment device.

Using a treated water enlarged in its cluster in comparison with a normal city water as an untreated water, a germination test for radish sprouts was carried out as follows:

(1) Preparation (a) Seed
60 seeds of radish sprouts made by Taiki Shubyo Kabushiki Kaisha were used.
(b) Water for Germination and Seedling
  i) City Water (as an untreated water)
  ii) Treated Water
  A city water and 30 seeds were put into a heat-resistant cup, and a magnetic force was irradiated from a side surface of the cup for 30 minutes by using the water treatment device shown in FIG. 1 (Preparation of a treated water and treated seeds).
(c) Formation of Germination and Seedling Bed
  i) City Water
  As shown in FIG. 11, an absorbent cotton 52 in a cut condition was put into a plastic container 50, and the city water as the untreated water was put into the container 50 till a water level of 15 mm from the bottom of the container 50. Further, the 30 untreated seeds were regularly arranged on the absorbent cotton 52 submerged in the untreated water.
  ii) Treated Water
  Similarly to the case of the untreated water, the treated water was put into the container 50, and the 30 treated seeds were regularly arranged in the treated water.
(d) Place for Germination and Seedling
Near a south window in a room (at a height of man's waist)
(e) Sunlight Receiving Time
  8:00 am–12:00 am
(f) Duration of the Test
  14 days
(g) Temperature Change
  12°–23° C.

(2) Progress

In the duration of 14 days from the start to the end of the test, the city water and the treated water were appropriately added into the container so that the seeds were submerged in the water. As compared with the untreated seeds in the city water, the treated seeds in the treated water absorbed the water more quickly, so that it was necessary to add the treated water in an amount about 2-3 times that of the city water.

In average, a seedling speed of the treated seeds in the treated water was higher than that of the untreated seeds in the city water.

(3) Results

After the 14-days test, lengths and weights of rhizomes of the radish sprouts were measured in the next day. The results of measurement are as follows:

Lengths i) Average length of the 30 radish sprouts grown in the city water was about 5 cm.
ii) Average length of the 30 radish sprouts grown in the treated water was about 6.5 cm.

Weights i) Total weight of the 30 radish sprouts grown in the city water was about 10 g.
ii) Total weight of the 30 radish sprouts grown in the treated water was about 15 g.

(4) Analysis

As apparent from the above results, the use of the treated water obtained by treating a city water contributes to quickness of growing by about 50% in terms of weight as compared with the use of the city water. This means a special effect of the water treatment device 1 according to the preferred embodiment.

Other Effects of the Water Treatment Device

It was observed that a treated water treated by the water treatment device has the following other effects.

(1) Taste Effects

In case of using the treated water as a drinking water, the taste of the drinking water became good. Further, in case of cooking with use of the treated water, the taste of the cooks became also good.

(2) Biological Effects

In case of ingesting the treated water as a drinking water or a content in cooks for a relatively long term (e.g., one month or more), the following biological effects were observed.
(a) Bleeding from a gum was suppressed.
(b) Falling of hair was reduced.
(c) A blood pressure became stable.
(d) Feces of human being and other animals became yellowish, and bad smell thereof almost disappeared. As to house pet dogs, an offensive odor (mainly ammonia odor) in a house remarkably decreased.

(3) The other effects

Rusting of iron was remarkably suppressed. A rusting test was carried out by immersing the same iron piece in the city water and the treated water and allowing it to stand for several days. In the fourth day after the start of the rusting test, the iron piece in the city water was completely rusted to such a degree that its color was generally changed into reddish brown. In contrast, the iron piece in the treated water was somewhat rusted in a proportion of about ¼ of the whole.

Figure 13:
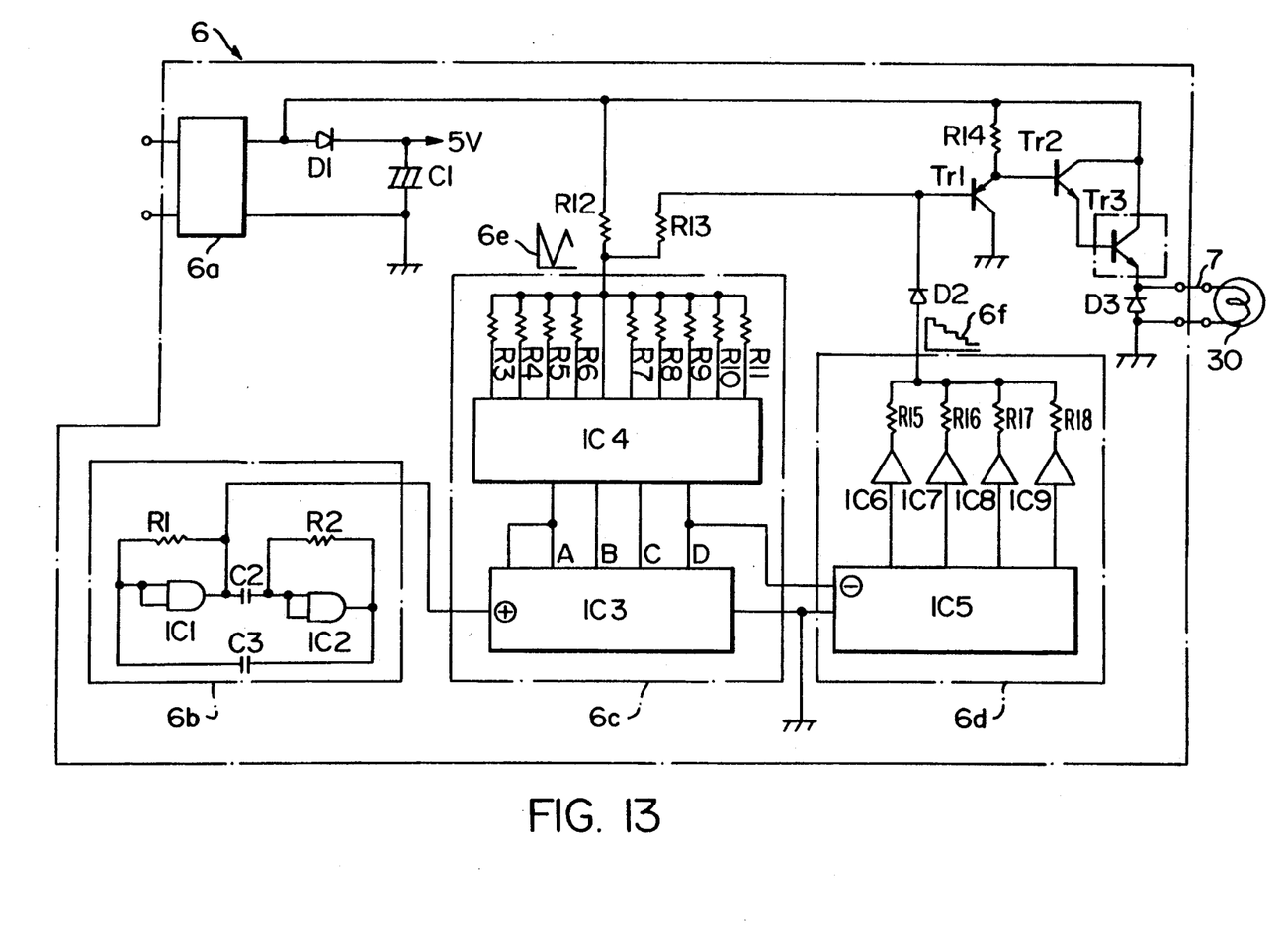
FIG. 13 is a circuit diagram of a control unit according to a second preferred embodiment of the present invention.

FIG. 13 shows a circuit construction of a second preferred embodiment of the present invention. In the second preferred embodiment, an incandescent lamp 30 is substituted for the coil 2 shown in FIG. 3. A light strength of the incandescent lamp 30 is controlled by the control unit 6 to change with any pattern shown in FIGS. 6A to 6D. Infrared rays of light from the incandescent lamp 30 is irradiated to water to be treated. Although not shown, the coil 2 shown in FIGS. 4 and 5 may be, of course, replaced by the incandescent lamp 30. Also in the second preferred embodiment, substantially the same effect of the water treatment as that in the first preferred embodiment was obtained. That is, enlargement of a water cluster was effected, but the effect was quantitatively just smaller than that in the first preferred embodiment.

Figure 14:
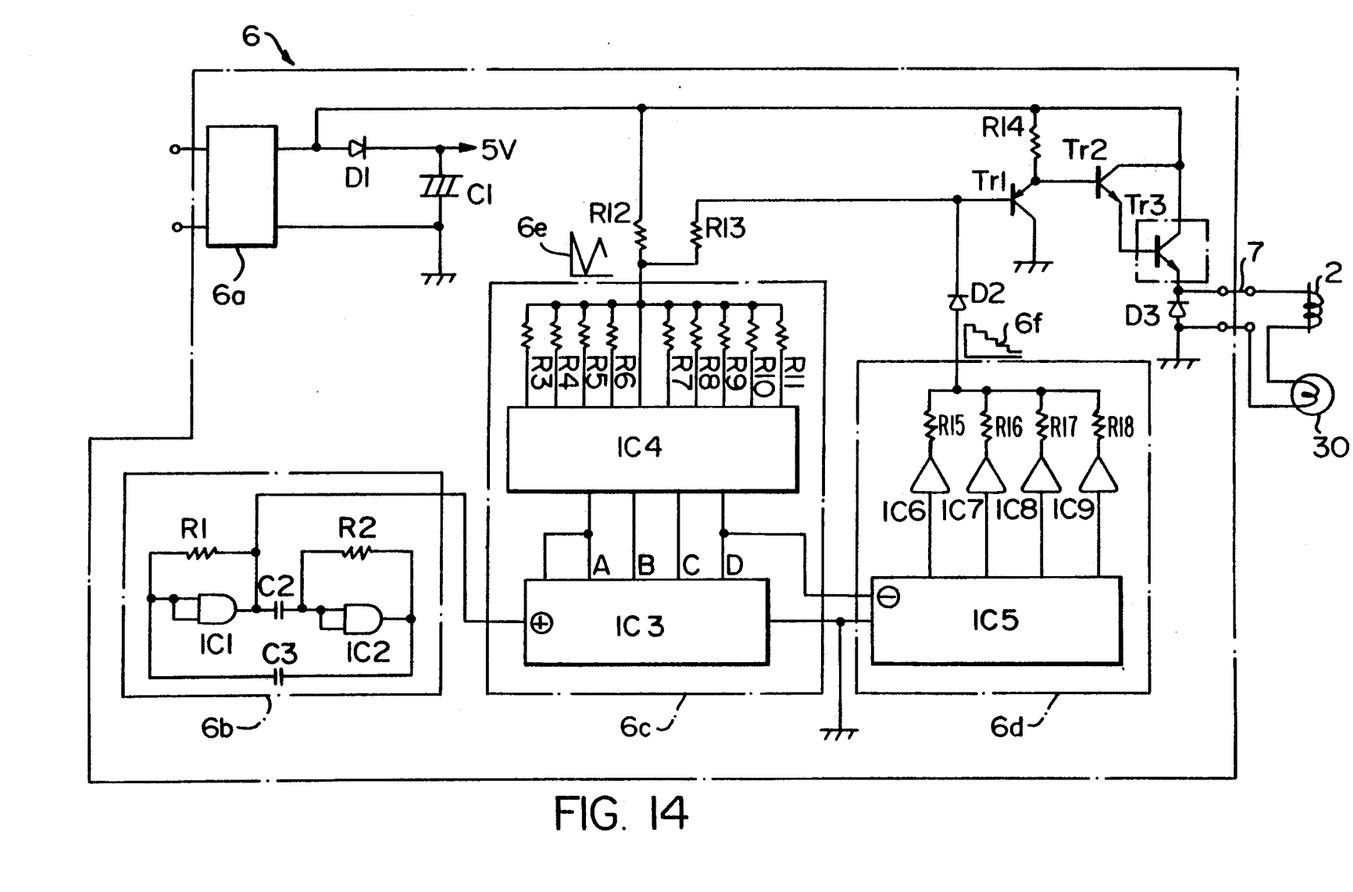
FIG. 14 is a circuit diagram of a control unit according to a third preferred embodiment of the present invention.
Figure 15:
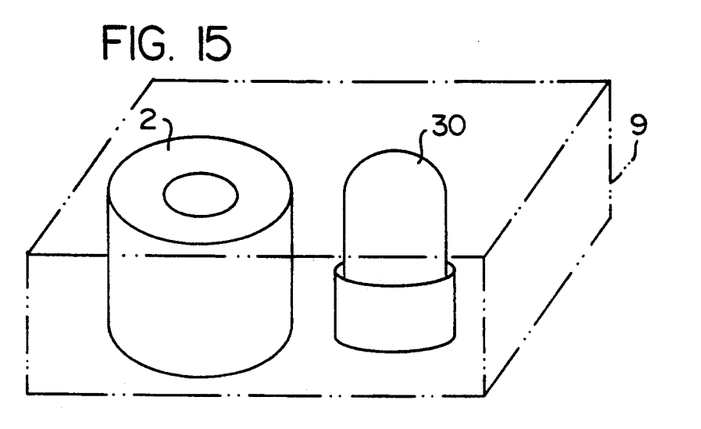
FIG. 15 is a schematic perspective view of a body in the third preferred embodiment shown in FIG. 14.
Figure 16:
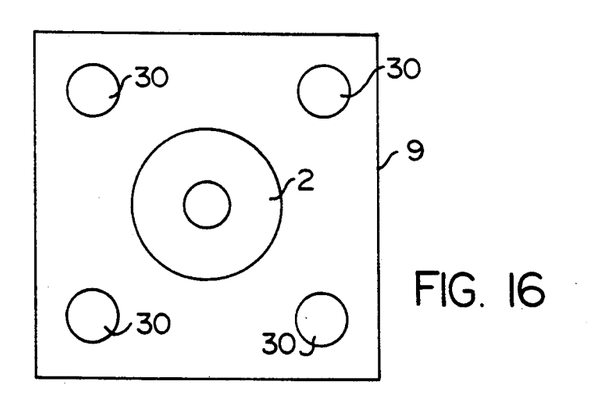
FIG. 16 is a plan view of a modification of the body in the third preferred embodiment.

FIG. 14 shows a circuit construction of a third preferred embodiment of the present invention. In the third preferred embodiment, the incandescent lamp 30 is connected in series with the coil 2. FIG. 15 shows a concrete example of juxtaposed arrangement of the coil 2 and the incandescent lamp 30 corresponding to the third preferred embodiment. Alternatively, as shown in FIG. 16, a plurality of incandescent lamps 30 may be arranged around the coil 2. It is to be understood that these examples of arrangement are merely illustrative and various modifications may be made.

Further, while the target irradiating device of the present invention is preferably adapted to water treatment as hereinbefore described, it is also effective for a remedy to a living body such as a human body. For example, when a magnetic force of light having the waveform pattern shown in FIG. 6A or 6B was irradiated to the stiff shoulder of a patient repeatedly several times, the stiffness of the shoulder was almost cured. Further, such a medical treatment effect was also confirmed in lumbago, neuralgia, etc.

While the invention has been described with reference specific embodiments, the description is illustrative and is not to be construed as limiting the scope of the invention. Various modifications and changes may occur to those skilled in the art without departing from the spirit and scope of the invention as defined by the appended claims.

What is claimed is:

1. A target irradiating device comprising:
   magnetic force generating means for electrically generating a magnetic force;
   power supplying means for supplying a driving power to said magnetic force generating means;
   control means for controlling said power supplying means so that a voltage signal for periodically changing an intensity of said magnetic force is supplied from said power supplying means, said voltage signal having a lowering pattern in one cycle such that a bottom point of voltage gradually lowers in terms of time with a top point of voltage maintained at a constant level; and
   an irradiating member for irradiating said magnetic force generated by said magnetic force generating means to a desired target.

2. The target irradiating device as defined in claim 1, wherein said control means comprises a first circuit for generating a triangular wave voltage signal; a second circuit for generating a step form wave voltage signal having a lowering pattern; and a third circuit for synthesizing said triangular wave voltage signal generated by said first circuit with said step form wave voltage signal generated by said second circuit.

3. The target irradiating device as defined in claim 2, wherein said control means comprising an oscillator for generating a triangular wave or sine wave voltage signal and a rectangular wave voltage signal; a multi-digit counter for accumulating the number of rectangular waves of said rectangular wave voltage signal; a D/A converter for D/A converting an output value from said counter to generate a step form wave voltage signal having a lowering pattern; a synthesizing circuit for synthesizing said triangular wave or sine wave voltage signal generated by said oscillator with said step form wave voltage signal generated by said D/A converter; and an amplifier for amplifying an output signal from said synthesizing circuit.

4. The target irradiating device as defined in claim 3, wherein said control means comprising an oscillator for generating a triangular wave or sine wave voltage signal and a rectangular wave voltage signal; a multi-digit counter for accumulating the number of rectangular waves of said rectangular wave voltage signal; a D/A converter for D/A converting an output value from said counter to generate a step form wave voltage signal having a lowering pattern; a synthesizing circuit for synthesizing said triangular wave or sine wave voltage signal generated by said oscillator with said step form wave voltage signal generated by said D/A converter; and an amplifier for amplifying an output signal from said synthesizing circuit.

5. The target irradiating device as defined in claim 1, wherein said target irradiating device is a water treatment device for treating water as said desired target by irradiating said magnetic force to said water.

6. The target irradiating device as defined in claim 5, wherein said water is treated by said water treatment device in a condition of natural convection.

7. The target irradiating device as defined in claim 5, wherein said water is treated by said water treatment device in a stirred condition with use of stirring means.

8. The target irradiating device as defined in claim 5, wherein said stirring means comprises a stirring screw adapted to be rotated.

9. The target irradiating device as defined in claim 2, wherein said stirring means comprises an elastic member and a movable magnetic plate separatably mounted on said elastic member, said movable magnetic plate being adapted to be driven by said magnetic force generating means, whereby when said magnetic force is generated, said movable magnetic plate is moved against an elastic force of said elastic member, while when said magnetic force is eliminated or reduced, said movable magnetic plate is returned to an original position by said elastic force of said elastic member.

10. A target irradiating device comprising:
    light generating means for electrically generating light; power supplying means for supplying a driving power to said light generating means;
    control means for controlling said power supplying means so that a voltage signal for periodically change an intensity of said light is supplied from said power supplying means, said voltage signal having a rising pattern in one cycle such that a bottom point of voltage gradually rises in terms of time with a top point of voltage maintained at a constant level; and
    an irradiating member for irradiating said light generated by said light generating means to a desired target.

11. The target irradiating device as defined in claim 10, wherein said control means comprises a first circuit for generating a triangular wave voltage signal; a second circuit for generating a step form wave voltage signal having a lowering pattern; and a third circuit for synthesizing said triangular wave voltage signal generated by said first circuit with said step form wave voltage signal generated by said second circuit.

12. The target irradiating device as defined in claim 10, wherein said target irradiating device is a water treatment device for treating water as said desired target by irradiating said magnetic force to said water.

13. The target irradiating device as defined in claim 12, wherein said water is treated by said water treatment device in a condition of natural convection.

14. The target irradiating device as defined in claim 12, wherein said water is treated by said water treatment device in a stirred condition with use of stirring means.

15. The target irradiating device as defined in claim 14, wherein said stirring means comprises a stirring screw adapted to be rotated.

* * * * *